(12) United States Patent
Yang et al.

(10) Patent No.: US 10,005,758 B2
(45) Date of Patent: Jun. 26, 2018

(54) PROCESS FOR THE PREPARATION OF 3-(3-CHLORO-1H-PYRAZOL-1-YL)PYRIDINE

(71) Applicant: Dow AgroSciences LLC, Indianapolis, IN (US)

(72) Inventors: Qiang Yang, Zionsville, IN (US); Beth Lorsbach, Indianapolis, IN (US); David E. Podhorez, Midland, MI (US)

(73) Assignee: Dow AgroSciences LLC, Indianapolis, IN (US)

(*) Notice: Subject to any disclaimer, the term of this patent is extended or adjusted under 35 U.S.C. 154(b) by 0 days. days.

(21) Appl. No.: 15/783,108

(22) Filed: Oct. 13, 2017

(65) Prior Publication Data
US 2018/0037565 A1 Feb. 8, 2018

Related U.S. Application Data

(60) Division of application No. 15/335,809, filed on Oct. 27, 2016, now Pat. No. 9,809,570, which is a division of application No. 14/811,246, filed on Jul. 28, 2015, now Pat. No. 9,522,900, which is a continuation of application No. 14/666,812, filed on Mar. 24, 2015, now Pat. No. 9,115,115, which is a division of application No. 14/517,344, filed on Oct. 17, 2014, now Pat. No. 9,024,031.

(60) Provisional application No. 62/039,128, filed on Aug. 19, 2014.

(51) Int. Cl.
C07D 401/04 (2006.01)

(52) U.S. Cl.
CPC .................. *C07D 401/04* (2013.01)

(58) Field of Classification Search
CPC .................................................... C07D 401/04
USPC .................................................... 546/276.1
See application file for complete search history.

(56) References Cited

U.S. PATENT DOCUMENTS

| | | |
|---|---|---|
| 3,597,341 A | 8/1971 | Oswald |
| 4,080,457 A | 3/1978 | Harrison et al. |
| 4,260,765 A | 4/1981 | Harrison et al. |
| 4,347,251 A | 8/1982 | Joseph et al. |
| 4,407,803 A | 10/1983 | Haviv et al. |
| 4,536,506 A | 8/1985 | Marcoux et al. |
| 4,556,671 A | 12/1985 | Copp et al. |
| 4,734,125 A | 3/1988 | Gehring et al. |
| 4,810,719 A | 3/1989 | Appleton et al. |
| 4,824,953 A | 4/1989 | Bronn |
| 5,220,028 A | 6/1993 | Iwasawa et al. |
| 5,625,074 A | 4/1997 | Daum et al. |
| 5,631,380 A | 5/1997 | Haas et al. |
| 5,652,372 A | 7/1997 | Muller et al. |
| 5,693,657 A | 12/1997 | Lee et al. |
| 5,750,718 A | 5/1998 | Muller et al. |
| 5,817,677 A | 10/1998 | Linz et al. |
| 5,854,264 A | 12/1998 | Anthony et al. |
| 5,854,265 A | 12/1998 | Anthony et al. |
| 5,869,681 A | 2/1999 | Muller et al. |
| 6,040,331 A | 3/2000 | Yamamoto et al. |
| 6,218,418 B1 | 4/2001 | Pevarello et al. |
| 6,413,984 B1 | 7/2002 | Philippo et al. |
| 6,506,747 B1 | 1/2003 | Betageri et al. |
| 6,548,525 B2 | 4/2003 | Galemmo, Jr. et al. |
| 6,720,427 B2 | 4/2004 | Sanner et al. |
| 6,878,196 B2 | 4/2005 | Harada et al. |
| 6,916,927 B2 | 7/2005 | Bunnage et al. |
| 6,965,032 B2 | 11/2005 | Freudenberger et al. |
| 7,192,906 B2 | 3/2007 | Hirohara et al. |
| 7,196,104 B2 | 3/2007 | Askew, Jr. et al. |
| 7,319,108 B2 | 1/2008 | Scwink et al. |
| 7,774,978 B2 | 8/2010 | Ding et al. |
| 7,803,832 B2 | 9/2010 | Critcher et al. |
| 7,910,606 B2 | 3/2011 | Nazere et al. |
| 7,923,573 B2 | 4/2011 | Tamaki et al. |
| 8,163,756 B2 | 4/2012 | Flynn et al. |
| 8,222,280 B2 | 7/2012 | Liu et al. |
| 8,901,153 B2 | 12/2014 | Buysse et al. |
| 9,024,031 B1 | 5/2015 | Yang et al. |
| 9,029,554 B1 | 5/2015 | Yang et al. |
| 9,029,555 B1 | 5/2015 | Li et al. |
| 9,029,556 B1 | 5/2015 | Yang et al. |

(Continued)

FOREIGN PATENT DOCUMENTS

| | | |
|---|---|---|
| CN | 87107798 | 5/1988 |
| CN | 1339027 | 3/2002 |
| CN | 1373662 | 10/2002 |
| CN | 1852885 A | 10/2006 |
| CN | 1307161 C | 3/2007 |
| CN | 101228134 | 7/2008 |
| EP | 0097323 | 1/1984 |
| EP | 0190457 | 8/1986 |
| EP | 0205024 | 12/1986 |
| EP | 0232538 | 8/1987 |

(Continued)

OTHER PUBLICATIONS

Ross, John R. et al. "Synthesis of 7-Substituted 5,6-Dimethyl-2,4-dioxo-1,2,4,7-tetrahydropyrrolo[2,3-d][1,3]oxazines", Synthesis, v. 1985, No. 8, Jan. 1, 1985, pp. 796-798.

(Continued)

*Primary Examiner* — Patricia L Morris
(74) *Attorney, Agent, or Firm* — Carl D. Corvin; Barnes & Thornburg LLP

(57) ABSTRACT

3-(3-chloro-1H-pyrazol-1-yl)pyridine is prepared by cyclizing 3-hydrazinopyridine-.dihydrochloride with a dialkyl maleate to provide an alkyl 5-oxo-2-(pyridin-3-yl)pyrazolidine-3-carboxylate, by chlorinating to provide an alkyl 3-chloro-1-(pyridin-3-yl)-4,5-dihydro-1H-pyrazole-5-carboxylate, by oxidizing to provide an alkyl 3-chloro-1-(pyridin-3-yl)-1H-pyrazole-5-carboxylate, by converting the ester to the carboxylic acid by hydrolysis to provide 3-chloro-1-(pyridin-3-yl)-1H-pyrazole-5-carboxylic acid hydrochloride, and by removing the carboxylic acid by a decarboxylation reaction.

11 Claims, No Drawings

(56) References Cited

U.S. PATENT DOCUMENTS

| | | |
|---|---|---|
| 9,044,017 B2 | 6/2015 | Yang et al. |
| 9,085,552 B1 | 7/2015 | Li et al. |
| 9,085,564 B2 | 7/2015 | Yang et al. |
| 9,102,654 B2 | 8/2015 | Yang et al. |
| 9,102,655 B2 | 8/2015 | Yang et al. |
| 9,108,932 B2 | 8/2015 | Ross et al. |
| 9,108,946 B2 | 8/2015 | Yang et al. |
| 9,115,115 B1 | 8/2015 | Yang et al. |
| 9,126,974 B2 | 9/2015 | Yang et al. |
| 9,156,813 B1 | 10/2015 | Li et al. |
| 9,174,962 B2 | 11/2015 | Yang et al. |
| 9,199,942 B2 | 12/2015 | Yang et al. |
| 9,199,964 B1 | 12/2015 | Yang et al. |
| 9,249,122 B1 | 2/2016 | Yang et al. |
| 9,255,081 B1 | 2/2016 | Li et al. |
| 9,255,082 B2 | 2/2016 | Yang et al. |
| 9,255,083 B2 | 2/2016 | Yang et al. |
| 9,260,396 B2 | 2/2016 | Yang et al. |
| 9,371,310 B2 | 6/2016 | Yang et al. |
| 9,414,594 B2 | 8/2016 | Yang et al. |
| 9,422,265 B2 | 8/2016 | Li et al. |
| 9,433,215 B2 | 9/2016 | Yang et al. |
| 9,434,712 B2 | 9/2016 | Yang et al. |
| 9,447,048 B2 | 9/2016 | Yang et al. |
| 9,522,900 B2 | 12/2016 | Yang et al. |
| 9,540,342 B2 | 1/2017 | Yang et al. |
| 9,550,751 B2 | 1/2017 | Yang et al. |
| 9,573,931 B2 | 2/2017 | Yang et al. |
| 9,580,403 B2 | 2/2017 | Li et al. |
| 9,580,405 B2 | 2/2017 | Yang et al. |
| 9,604,942 B2 | 3/2017 | Ross et al. |
| 9,611,247 B2 | 4/2017 | Yang et al. |
| 9,661,849 B2 | 5/2017 | Yang et al. |
| 9,663,489 B2 | 5/2017 | Li et al. |
| 9,670,164 B2 | 6/2017 | Yang et al. |
| 9,670,178 B2 | 6/2017 | Yang et al. |
| 9,723,839 B2 | 8/2017 | Yang et al. |
| 9,796,682 B2 | 10/2017 | Yang et al. |
| 9,809,570 B2 | 11/2017 | Yang et al. |
| 9,840,490 B2 | 12/2017 | Li et al. |
| 9,862,702 B2 | 1/2018 | Yang et al. |
| 2002/0013326 A1 | 1/2002 | Tiebes et al. |
| 2003/0153464 A1 | 8/2003 | Nakamura et al. |
| 2003/0213405 A1 | 11/2003 | Harada et al. |
| 2004/0043904 A1 | 3/2004 | Yamaguchi et al. |
| 2004/0082629 A1 | 4/2004 | Iwataki et al. |
| 2004/0255397 A1 | 12/2004 | Fessman et al. |
| 2005/0038059 A1 | 2/2005 | Mueller et al. |
| 2005/0176710 A1 | 8/2005 | Schwink et al. |
| 2006/0135778 A1 | 6/2006 | Schnatterer et al. |
| 2006/0160857 A1 | 7/2006 | Buettelmann et al. |
| 2006/0160875 A1 | 7/2006 | Gaines et al. |
| 2006/0167020 A1 | 7/2006 | Dickerson et al. |
| 2006/0287365 A1 | 12/2006 | Billen et al. |
| 2006/0287541 A1 | 12/2006 | Nishino et al. |
| 2007/0049604 A1 | 3/2007 | Nam et al. |
| 2007/0167426 A1 | 7/2007 | Siddiqui et al. |
| 2008/0004301 A1 | 1/2008 | Tamaki et al. |
| 2008/0027046 A1 | 1/2008 | Annan et al. |
| 2009/0023709 A1 | 1/2009 | Gillespie et al. |
| 2009/0069288 A1 | 3/2009 | Breinlinger et al. |
| 2009/0137524 A1 | 5/2009 | Billen et al. |
| 2009/0275592 A1 | 11/2009 | Zeng et al. |
| 2009/0325956 A1 | 12/2009 | Taniguchi et al. |
| 2010/0130474 A1 | 5/2010 | Bothmann et al. |
| 2010/0204164 A1 | 8/2010 | Crouse et al. |
| 2010/0286169 A1 | 11/2010 | Guiles et al. |
| 2010/0292253 A1 | 11/2010 | Trullinger et al. |
| 2010/0305200 A1 | 12/2010 | Velicelebi et al. |
| 2011/0021771 A1 | 1/2011 | Mallais et al. |
| 2011/0048261 A1 | 3/2011 | Shimura |
| 2011/0098287 A1 | 4/2011 | Bretschneider et al. |
| 2011/0118290 A1 | 5/2011 | Bretschneider et al. |
| 2011/0166129 A1 | 7/2011 | MacHacek et al. |
| 2011/0166143 A1 | 7/2011 | Bretschneider et al. |
| 2011/0184188 A1 | 7/2011 | Wade et al. |
| 2011/0201649 A1 | 8/2011 | Matsuzaki et al. |
| 2011/0212949 A1 | 9/2011 | Bretschneider et al. |
| 2011/0275583 A1 | 11/2011 | Bretschneider et al. |
| 2011/0319428 A1 | 12/2011 | Fuβlein et al. |
| 2012/0053146 A1 | 3/2012 | Parker et al. |
| 2012/0094837 A1 | 4/2012 | Muhlthau et al. |
| 2012/0095023 A1 | 4/2012 | Bretschneider et al. |
| 2012/0101294 A1 | 4/2012 | Hirota et al. |
| 2012/0110701 A1 | 5/2012 | Garizi et al. |
| 2012/0110702 A1 | 5/2012 | Yap et al. |
| 2012/0115811 A1 | 5/2012 | Du et al. |
| 2012/0165345 A1 | 6/2012 | Bretschneider et al. |
| 2012/0172218 A1 | 7/2012 | Crouse et al. |
| 2012/0220453 A1 | 8/2012 | Lowe et al. |
| 2012/0252770 A1 | 10/2012 | Berger et al. |
| 2013/0019348 A1 | 1/2013 | Crouse et al. |
| 2013/0072382 A1 | 3/2013 | Trullinger et al. |
| 2013/0089622 A1 | 4/2013 | Trullinger et al. |
| 2013/0109566 A1 | 5/2013 | Niyaz et al. |
| 2013/0261141 A1 | 10/2013 | Bretschneider et al. |
| 2013/0288893 A1 | 10/2013 | Buysse et al. |
| 2013/0291227 A1 | 10/2013 | Buysse et al. |
| 2013/0324736 A1 | 12/2013 | Ross, Jr. et al. |
| 2013/0324737 A1 | 12/2013 | Ross, Jr. et al. |
| 2013/0338367 A1 | 12/2013 | Numata et al. |
| 2014/0162874 A1 | 6/2014 | Yap et al. |
| 2015/0112076 A1 | 4/2015 | Yang et al. |
| 2015/0252016 A1 | 9/2015 | Yang et al. |
| 2016/0152593 A1 | 6/2016 | Li et al. |
| 2017/0044134 A1 | 2/2017 | Yang et al. |
| 2017/0081288 A1 | 3/2017 | Yang et al. |
| 2017/0101392 A1 | 4/2017 | Yang et al. |
| 2017/0101393 A1 | 4/2017 | Li et al. |
| 2017/0215420 A1 | 8/2017 | Yang et al. |
| 2017/0217924 A1 | 8/2017 | Li et al. |
| 2017/0226078 A1 | 8/2017 | Yang et al. |
| 2017/0233367 A1 | 8/2017 | Yang et al. |
| 2017/0295786 A1 | 10/2017 | Yang et al. |

FOREIGN PATENT DOCUMENTS

| | | |
|---|---|---|
| EP | 0248315 | 12/1987 |
| EP | 0425948 | 5/1991 |
| EP | 0273549 | 1/1992 |
| EP | 0757987 A1 | 2/1997 |
| EP | 1273582 | 1/2003 |
| EP | 1321463 | 6/2003 |
| EP | 1329160 | 7/2003 |
| EP | 1757590 A1 | 2/2007 |
| JP | 1987-153273 | 7/1987 |
| JP | 1988-174905 | 7/1988 |
| JP | 1989-226815 | 9/1989 |
| JP | 2003-212864 | 7/2003 |
| JP | 2004-051628 | 2/2004 |
| JP | 2004-292703 | 10/2004 |
| JP | 2012-188418 | 10/2012 |
| JP | 2013-075871 | 4/2013 |
| JP | 2013-082699 | 5/2013 |
| JP | 2013-082704 | 5/2013 |
| JP | 2013-107867 | 6/2013 |
| JP | 2013-129651 | 7/2013 |
| JP | 2013-129653 | 7/2013 |
| WO | 1994/013644 | 6/1994 |
| WO | 1997/036897 | 10/1997 |
| WO | 1998/049166 | 11/1998 |
| WO | 2000/035919 | 6/2000 |
| WO | 2001/12189 | 2/2001 |
| WO | 2001/034127 | 5/2001 |
| WO | 2001/090078 | 11/2001 |
| WO | 2002/083111 | 10/2002 |
| WO | 2003/008405 | 1/2003 |
| WO | 2003/072102 | 9/2003 |
| WO | 2004/041813 | 5/2004 |
| WO | 2005/070925 | 8/2005 |
| WO | 2005/074875 | 8/2005 |
| WO | 2006/023462 | 3/2006 |
| WO | 2006/033005 | 3/2006 |
| WO | 2006/046593 | 5/2006 |

(56) References Cited

FOREIGN PATENT DOCUMENTS

| WO | 2006/103045 | 10/2006 |
|---|---|---|
| WO | 2007/005838 | 1/2007 |
| WO | 2008/090382 | 7/2007 |
| WO | 2007/087427 | 8/2007 |
| WO | 2007/098826 | 9/2007 |
| WO | 2008/005457 | 1/2008 |
| WO | 2008//079277 | 7/2008 |
| WO | 2009/149858 | 12/2009 |
| WO | 2010/006713 | 1/2010 |
| WO | 2010/009290 | 1/2010 |
| WO | 2010/012442 | 2/2010 |
| WO | 2010/033360 | 3/2010 |
| WO | 2010/048207 | 4/2010 |
| WO | 2010/060379 | 6/2010 |
| WO | 2010/075376 | 7/2010 |
| WO | 2010/129497 | 11/2010 |
| WO | 2010/133336 | 11/2010 |
| WO | 2010/146236 | 12/2010 |
| WO | 2011/003065 | 1/2011 |
| WO | 2011/043371 | 4/2011 |
| WO | 2011/045224 | 4/2011 |
| WO | 2011/045240 | 4/2011 |
| WO | 2011/091153 | 7/2011 |
| WO | 2011/101229 | 8/2011 |
| WO | 2011/126903 | 10/2011 |
| WO | 2011/128304 | 10/2011 |
| WO | 2011/134964 | 11/2011 |
| WO | 2011/138285 | 11/2011 |
| WO | 2011/163518 | 12/2011 |
| WO | 2012/000896 | 1/2012 |
| WO | 2012/004217 | 1/2012 |
| WO | 2012/007500 | 1/2012 |
| WO | 2010/035011 | 3/2012 |
| WO | 2012/052412 | 4/2012 |
| WO | 2012/061290 | 5/2012 |
| WO | 2012/070114 | 5/2012 |
| WO | 2012/102387 | 8/2012 |
| WO | 2012/108511 | 8/2012 |
| WO | 2012/147107 | 11/2012 |
| WO | 2012/168361 | 12/2012 |
| WO | 2013/000931 | 1/2013 |
| WO | 2013/010946 | 1/2013 |
| WO | 2013/010947 | 1/2013 |
| WO | 2013/062980 | 5/2013 |
| WO | 2013/062981 | 5/2013 |
| WO | 2013/064324 | 5/2013 |
| WO | 2013/156431 | 10/2013 |
| WO | 2013/156433 | 10/2013 |
| WO | 2013/162716 | 10/2013 |
| WO | 2015/058020 | 4/2015 |
| WO | 2015/058022 | 4/2015 |
| WO | 2015/058023 | 4/2015 |
| WO | 2015/058024 | 4/2015 |
| WO | 2015/058026 | 4/2015 |
| WO | 2015/058028 | 4/2015 |

OTHER PUBLICATIONS

Lahm et al., "Rynaxypyr™: A new insecticidal anthranilic diamide that acts as a potent and selective ryanodine receptor activator," Biorg. Med. Chem. Lett., 2007, 17, 6274-6279.
Giornal, F. et al., "A New Synthesis and Process Development of Bis(fluoroalkyl)pyrazoles As Novel Agrophores," Organic Process Research and Development, 2014, 18, 1002-1009.
Lieser, T. et al., "Artificial organic high polymers, VII, New acrylyl derivatives and their polymerization products," Chemische Berichte, VCH, DE, 1951, 84, 4-12.
Tanaka, N. et al., "Synthesis of pyrazole carboxylic acid via cobalt-catalyzed phase oxidation," Chemistry Letters, Chemical Society of Japan, 1991, 4, 585-588.
Kempe et al., "Responsive Glyco-poly(2-oxaoline)s: Synthesis, Cloud Point Tuning, and Lectin Binding," Biomacromolecules 2011, vol. 12, pp. 2591-2600.
Fields et al., "Preparation of Trifluoromethyl-Pyrazoles and—Pyrazolines by the Reaction of 2,2,2-Trifluorodiazoethane with Carbon-Carbon Multiple Bonds," Journal of Fluorine Chemistry, 1979, vol. 13, pp. 147-158.
Bradbury et al., "Enzyme-catalysed peptide amidation," Eur. J. Biochem. 1987, vol. 169, pp. 579-584.
International Search Report and Written Opinion for PCT/US2014/061005 dated Dec. 16, 2014.
International Search Report and Written Opinion for PCT/US2014/061006 dated Dec. 8, 2014.
International Search Report and Written Opinion for PCT/US2014/061007 dated Dec. 31, 2014.
International Search Report and Written Opinion for PCT/US2014/061009 dated Dec. 8, 2014.
International Search Report and Written Opinion for PCT/US2014/061010 dated Dec. 15, 2014.
International Search Report and Written Opinion for PCT/US2014/061012 dated Dec. 15, 2014.
International Search Report and Written Opinion for PCT/US2014/061014 dated Dec. 15, 2014.
International Search Report and Written Opinion for PCT/US2014/061016 dated Dec. 15, 2014.
International Search Report and Written Opinion for PCT/US2014/061022 dated Dec. 29, 2014.
International Search Report and Written Opinion for PCT/US2014/061023 dated Dec. 15, 2014.
International Search Report and Written Opinion for PCT/US2014/061024 dated Dec. 15, 2014.
International Search Report and Written Opinion for PCT/US2014/061027 dated Dec. 15, 2014.
International Search Report and Written Opinion for PCT/US2014/061029 dated Dec. 15, 2014.
International Search Report and Written Opinion for PCT/US2014/061030 dated Dec. 15, 2014.
International Search Report and Written Opinion for PCT/US2013/029615 dated May 8, 2013.
Ameduri, B. et al., "Synthesis and polymerization of fluorinated monomers bearing a reactive lateral group Part 4. Preparation of functional perfluorovinyl monomers by radical addition of functional mercaptans to 1,1,2-trifluoro-1,4-pentadiene." J. Fluorine Chemistry, 92, 77-84 (1998).
International Preliminary Report on Patentability for PCT/US2011/058578 dated Dec. 21, 2012.
International Search Report and Written Opinion for PCT/US2011/058578 dated Apr. 5, 2012.
Kadam, S.S. et al., "Synthesis and Tautomerism of Substituted Pyrazolo[4,3-c]pyrazoles." Eur. J. Chem., 6811-6822 (2013).
Gorelik; Zhumai Organicheskol khlml, 1980 (16), 1322, ABSTRACT, Chemical Abstracts, Accession No. 6206562.
National Center for Biotechnology Information, PubChem Compound Database; CID=17132489,https://pubchem.ncbi.nlm.nih.gov/compound/17132489, create date Nov. 13, 2007.
Frigola; European Journal of Medicinal Chemistry 1989, 435-445.
Binz et al. "Derivatives of pyridine, etc.," CA 25:30083 (1931).

PROCESS FOR THE PREPARATION OF 3-(3-CHLORO-1H-PYRAZOL-1-YL)PYRIDINE

CROSS REFERENCE TO RELATED APPLICATIONS

This application is a divisional of U.S. application Ser. No. 15/335,809 filed on Oct. 27, 2016, which is a divisional of U.S. application Ser. No. 14/811,246 filed on Jul. 28, 2015, which is a continuation of U.S. application Ser. No. 14/666,812 filed on Mar. 24, 2015, which is a divisional of U.S. application Ser. No. 14/517,344 filed on Oct. 17, 2014, which claims the benefit of U.S. Provisional Patent Application Ser. No. 62/039,128, filed Aug. 19, 2014, the entire disclosures of which are hereby expressly incorporated by reference in this Application.

BACKGROUND

The present invention concerns an improved process for preparing 3-(3-chloro-1H-pyrazol-1-yl)pyridine.

US 20130288893(A1) describes, inter alia, certain (3-halo-1-(pyridin-3-yl)-1H-pyrazol-4-yl)amides and carbamates and their use as pesticides. The route to prepare such compounds involved the preparation of 3-(3-chloro-1H-pyrazol-1-yl)pyridine by the direct coupling of 3-bromopyridine with 3-chloropyrazole. The 3-chloropyrazole was prepared by a) treating 1H-pyrazole with 2 dimethylsulfamoyl chloride and sodium hydride to provide N,N-dimethyl-1H-pyrazole-1-sulfonamide, b) treating the N,N-dimethyl-1H-pyrazole-1-sulfonamide with perchloroethane and n-butyl lithium to provide 3-chloro-N,N-dimethyl-1H-pyrazole-1-sulfonamide, and c) removing the N,N-dimethylsulfonamide from 3-chloro-N,N-dimethyl-1H-pyrazole-1-sulfonamide with trifluoroacetic acid to give the 3-chloropyrazole.

The disclosed process produces low yields, relies on a starting material that is difficult to prepare (3-chloropyrazole) and provides a product that is difficult to isolate in a pure form. It would be desirable to have a process for preparing 3-(3-chloro-1H-pyrazol-1-yl)pyridine that avoids these problems.

SUMMARY

The present invention provides such an alternative by cyclizing 3-hydrazinopyridine-.dihydrochloride with a dialkyl maleate to provide alkyl 5-oxo-2-(pyridin-3-yl)pyrazolidine-3-carboxylate (10a), by chlorinating to provide alkyl 3-chloro-1-(pyridin-3-yl)-4,5-dihydro-1H-pyrazole-5-carboxylate (10b), by oxidizing to provide alkyl 3-chloro-1-(pyridin-3-yl)-1H-pyrazole-5-carboxylate (10c), by converting the ester to the carboxylic acid by hydrolysis to provide 3-chloro-1-(pyridin-3-yl)-1H-pyrazole-5-carboxylic acid hydrochloride (10d), and by removing the carboxylic acid by a decarboxylation reaction. Thus, the present invention concerns a process for preparing 3-(3-chloro-1H-pyrazol-1-yl)pyridine (5b),

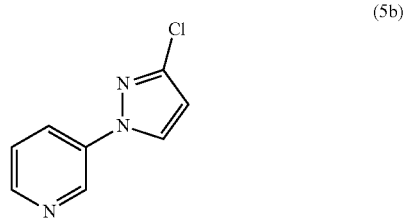 [SMILES: Clc1ccn(-c2cccnc2)n1]

which comprises a) treating 3-hydrazinopyridine.dihydrochloride

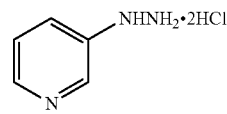

with a dialkyl maleate

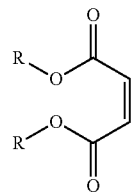

wherein

R represents $(C_1$-$C_4)$ alkyl, in a $(C_1$-$C_4)$ aliphatic alcohol at a temperature of about 25° C. to about 100° C. in the presence of an alkali metal $(C_1$-$C_4)$ alkoxide to provide an alkyl 5-oxo-2-(pyridin-3-yl)pyrazolidine-3-carboxylate (10a)

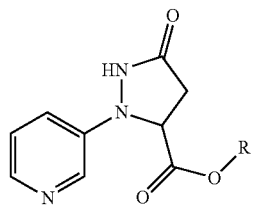

(10a)

wherein R is as previously defined;

b) treating the alkyl 5-oxo-2-(pyridin-3-yl)pyrazolidine-3-carboxylate (10a) with a chlorinating reagent in an inert organic solvent at a temperature of about 25° C. to about 100° C. to provide an alkyl 3-chloro-1-(pyridin-3-yl)-4,5-dihydro-1H-pyrazole-5-carboxylate (10b)

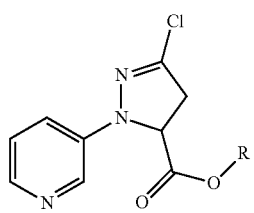

(10b)

wherein R is as previously defined;

c) treating the alkyl 3-chloro-1-(pyridin-3-yl)-4,5-dihydro-1H-pyrazole-5-carboxylate (10b) with an oxidant in an inert organic solvent at a temperature of about 25° C. to about 100° C. to provide an alkyl 3-chloro-1-(pyridin-3-yl)-1H-pyrazole-5-carboxylate (10c)

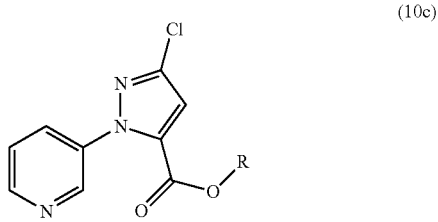

wherein R is as previously defined;

d) treating the alkyl 3-chloro-1-(pyridin-3-yl)-1H-pyrazole-5-carboxylate (10c) with aqueous hydrochloric acid at a temperature of about 25° C. to about 100° C. to provide 3-chloro-1-(pyridin-3-yl)-1H-pyrazole-5-carboxylic acid hydrochloride (10d)

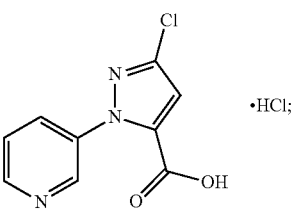

and e) treating 3-chloro-1-(pyridin-3-yl)-1H-pyrazole-5-carboxylic acid hydrochloride with copper(II) oxide in a polar aprotic solvent at a temperature of about 80° C. to about 140° C.

DETAILED DESCRIPTION

The present invention provides an improved process for preparing 3-(3-chloro-1H-pyrazol-1-yl)pyridine (5b), by cyclizing 3-hydrazinopyridine.dihydrochloride with a dialkyl maleate to provide an alkyl 5-oxo-2-(pyridin-3-yl)pyrazolidine-3-carboxylate (10a), by chlorinating to provide an alkyl 3-chloro-1-(pyridin-3-yl)-4,5-dihydro-1H-pyrazole-5-carboxylate (10b), by oxidizing to provide an alkyl 3-chloro-1-(pyridin-3-yl)-1H-pyrazole-5-carboxylate (10c), by converting the ester to the carboxylic acid by hydrolysis to provide 3-chloro-1-(pyridin-3-yl)-1H-pyrazole-5-carboxylic acid hydrochloride (10d), and by removing the carboxylic acid by a decarboxylation reaction.

In the first step, 3-hydrazinopyridine.dihydrochloride is treated with a dialkyl maleate in a ($C_1$-$C_4$) aliphatic alcohol at a temperature of about 25° C. to about 100° C. in the presence of an alkali metal ($C_1$-$C_4$) alkoxide to provide an alkyl 5-oxo-2-(pyridin-3-yl)pyrazolidine-3-carboxylate (10a). While stoichiometric amounts of 3-hydrazinopyridine.dihydrochloride and dialkyl maleate are required, it is often convenient to use about a 1.5 fold to about a 2 fold excess of dialkyl maleate. The cyclization is run in the presence of an alkali metal ($C_1$-$C_4$) alkoxide base. It is often convenient to use about a 2 fold to about a 5 fold excess of base. The cyclization is performed in a ($C_1$-$C_4$) aliphatic alcohol. It is most convenient that the alkoxide base, the alcohol solvent and the ester of the maleate be the same, for example, sodium ethoxide in ethanol with diethyl maleate.

In a preferred reaction, sodium ethoxide in an anhydrous ethanol are introduced into a reaction vessel and 3-hydrazinopyridine.dihydrochloride is added. The mixture is stirred and diethyl maleate is added. The mixture is heated at about 60° C. until most of the 3-hydrazinopyridine has reacted. The mixture is allowed to cool and the excess base is neutralized with acid. The crude ethyl 5-oxo-2-(pyridin-3-yl)pyrazolidine-3-carboxylate (10a) is conveniently isolated and purified by standard techniques.

In the second step, the alkyl 5-oxo-2-(pyridin-3-yl)pyrazolidine-3-carboxylate (10a) is treated with a chlorinating reagent in an inert organic solvent at a temperature of about 25° C. to about 100° C. to provide alkyl 3-chloro-1-(pyridin-3-yl)-4,5-dihydro-1H-pyrazole-5-carboxylate (10b). Suitable chlorinating reagents include phosphoryl chloride (phosphorous oxychloride) and phosphorus pentachloride. Phosphoryl chloride is preferred. It is often convenient to use about a 1.1 fold to about a 10 fold excess of the chlorinating reagent. The chlorination is performed in an organic solvent that is inert to the chlorinating reagent. Suitable solvents include nitriles such as acetonitrile. With phosphoryl chloride as the chlorinating reagent, acetonitrile is a preferred solvent.

In a preferred reaction, ethyl 5-oxo-2-(pyridin-3-yl)pyrazolidine-3-carboxylate (10a) and acetonitrile are mixed with phosphoryl chloride and the mixture is heated to about 60° C. for 2 hours. After the reaction is determined to be complete, the reaction is cooled to room temperature and diluted with water. The reaction mixture is then neutralized with base and extracted. The alkyl 3-chloro-1-(pyridin-3-yl)-4,5-dihydro-1H-pyrazole-5-carboxylate (10b) can be purified by standard techniques.

In the third step, alkyl 3-chloro-1-(pyridin-3-yl)-4,5-dihydro-1H-pyrazole-5-carboxylate (10b) is treated with an oxidant in an organic solvent at a temperature of about 25° C. to about 100° C. to provide alkyl 3-chloro-1-(pyridin-3-yl)-1H-pyrazole-5-carboxylate (10c). Suitable oxidants include manganese (IV) oxide and sodium persulfate/sulfuric acid. It is often convenient to use about a 1.5 fold to about a 15 fold excess of oxidant. The oxidation is performed in an organic solvent that is inert to the oxidant. Suitable solvents include nitriles such as acetonitrile. With manganese (IV) oxide or sodium persulfate/sulfuric acid as the oxidant, acetonitrile is a preferred solvent.

In a preferred reaction, ethyl 3-chloro-1-(pyridin-3-yl)-4,5-dihydro-1H-pyrazole-5-carboxylate (10b) and acetonitrile are mixed with manganese(IV) oxide and the mixture is heated at about 60° C. until the reaction is completed. The ethyl 3-chloro-1-(pyridin-3-yl)-1H-pyrazole-5-carboxylate (10c) is conveniently isolated and purified by standard techniques.

In the fourth step, alkyl 3-chloro-1-(pyridin-3-yl)-1H-pyrazole-5-carboxylate (10c) is then converted to the desired 3-chloro-1-(pyridin-3-yl)-1H-pyrazole-5-carboxylic acid hydrochloride (10d) by treatment in aqueous hydrochloric acid at a temperature of about 25° C. to about 100° C. While stoichiometric amounts of reagents are required, it is often convenient to use an excess of reagent with respect to the alkyl 3-chloro-1-(pyridin-3-yl)-1H-pyrazole-5-carboxylate (10c). Thus, aqueous hydrochloric acid is used in large excess as the reaction medium.

In a preferred reaction, a mixture of ethyl 3-chloro-1-(pyridin-3-yl)-1H-pyrazole-5-carboxylate (10c) and aqueous hydrochloric acid are mixed and heated to about 90° C. After completion of the reaction, the mixture is cooled and diluted with an organic solvent. The resulting solution is concentrated. The 3-chloro-1-(pyridin-3-yl)-1H-pyrazole-5-carboxylic acid hydrochloride (10d) can be purified by standard techniques such as filtration.

3-Chloro-1-(pyridin-3-yl)-1H-pyrazole-5-carboxylic acid hydrochloride (10d) is then converted to the desired 3-(3-chloro-1H-pyrazol-1-yl)pyridine (5b) by decarboxylation in the presence of copper (II) oxide in polar solvents at a temperature from about 80° C. to about 140° C. It was surprisingly discovered that this decarboxylation only occurs in the presence of copper (II) oxide. Several known decarboxylation agents from the literature such as, for example, hydrochloric acid (See Example 4), sulfuric acid (See "CE-5"), and palladium (II) trifluoroacetate/trifluoroacetic acid (See "CE-5") did not yield the desired product.

In a preferred reaction, a mixture of 3-chloro-1-(pyridin-3-yl)-1H-pyrazole-5-carboxylic acid hydrochloride (10d) and copper(II) oxide are mixed in an organic solvent and heated to about 120° C. It is often convenient to use less than stoichiometric amounts of copper(II) oxide. The decarboxylation is performed in a polar aprotic organic solvent. Suitable solvents include N,N'-dimethylformamide. After completion of the reaction, the mixture is cooled, diluted with ammonium hydroxide, and extracted. The 3-(3-chloro-1H-pyrazol-1-yl)pyridine (5b) can be purified by standard techniques.

The following examples are presented to illustrate the invention.

Examples

1. Preparation of Ethyl 5-oxo-2-(pyridin-3-yl)pyrazolidine-3-carboxylate (10a)

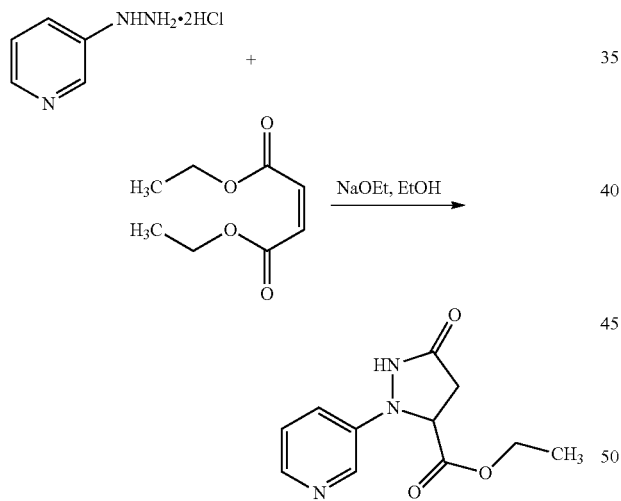

A 4-neck round bottomed flask (250 mL) was charged with sodium ethoxide (21 wt % in ethanol, 56 mL, 192 mmol). 3-Hydrazinopyridine.dihydrochloride (10.0 g, 55.0 mmol) was added, causing an exotherm from 20° C. to 32° C. The reaction was allowed to cool to 20° C. and diethyl maleate (13.4 mL, 82.0 mmol) was added, and the reaction was heated at 60° C. for 3 hours (h). The reaction was cooled to 20° C. and quenched with acetic acid. The reaction mixture was diluted with water (100 mL) and extracted with ethyl acetate (3×100 mL). The combined organics were concentrated to dryness and the residue was purified by flash column chromatography using ethyl acetate as eluent to the title compound as a blue oil (6.60 g, 51%): $^1$H NMR (400 MHz, DMSO-$d_6$) δ 10.40 (s, 1H), 8.40-8.26 (m, 1H), 8.19 (dd, J=4.4, 1.6 Hz, 1H), 7.47-7.21 (m, 2H), 4.77 (dd, J=9.8, 2.1 Hz, 1H), 4.22 (qd, J=7.1, 1.7 Hz, 2H), 3.05 (dd, J=17.0, 9.8 Hz, 1H), 1.99 (s, 1H), 1.25 (t, J=7.1 Hz, 3H); $^{13}$C NMR (101 MHz, DMSO-$d_6$) δ 170.37, 146.60, 142.60, 137.28, 123.54, 121.94, 65.49, 61.32, 32.15, 20.72, 13.94; ESIMS m/z 236 ([M+H]$^+$).

2. Preparation of Ethyl 3-chloro-1-(pyridin-3-yl)-4,5-dihydro-1H-pyrazole-5-carboxylate (10b)

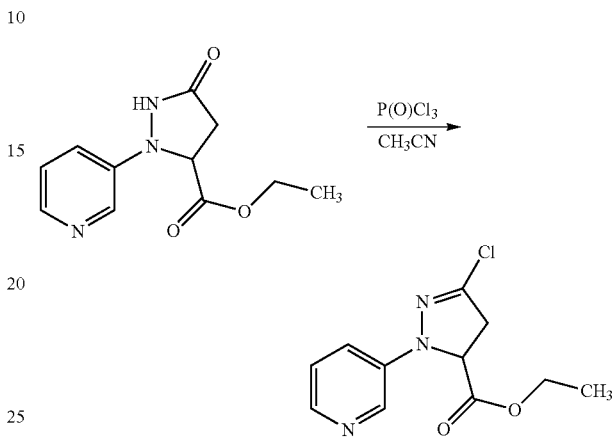

A 3-neck round bottomed flask (100 mL) was charged with ethyl 5-oxo-2-(pyridin-3-yl)pyrazolidine-3-carboxylate (8.50 g, 36.1 mmol) and acetonitrile (40 mL). Phosphoryl chloride (4.05 mL, 43.4 mmol) was charged and the reaction was heated at 60° C. for 2 h. The reaction was cooled to 20° C. and water (100 mL) was added. Sodium carbonate was added to adjust pH to 8 and the mixture was extracted with ethyl acetate (3×100 mL). The organic layers were concentrated to dryness and the residue was purified by flash column chromatography using 30-80% ethyl acetate/hexanes as eluent to provide the title compound as a yellow oil (7.30 g, 79%): $^1$H NMR (400 MHz, CDCl$_3$) δ 8.30 (dd, J=2.9, 0.8 Hz, 1H), 8.17 (dd, J=4.7, 1.4 Hz, 1H), 7.38 (ddd, J=8.4, 2.8, 1.4 Hz, 1H), 7.18 (ddd, J=8.4, 4.7, 0.7 Hz, 1H), 4.79 (dd, J=12.4, 6.9 Hz, 1H), 4.24 (qd, J=7.1, 1.1 Hz, 2H), 3.55 (dd, J=17.7, 12.4 Hz, 1H), 3.33 (dd, J=17.8, 6.9 Hz, 1H), 1.25 (t, J=7.1 Hz, 3H); $^{13}$C NMR (101 MHz, CDCl$_3$) δ 169.65, 141.90, 141.33, 141.09, 135.13, 123.53, 120.37, 62.89, 62.35, 42.45, 14.03; ESIMS m/z 254 ([M+H]$^+$).

3. Preparation of Ethyl 3-chloro-1-(pyridin-3-yl)-1H-pyrazole-5-carboxylate (10c)

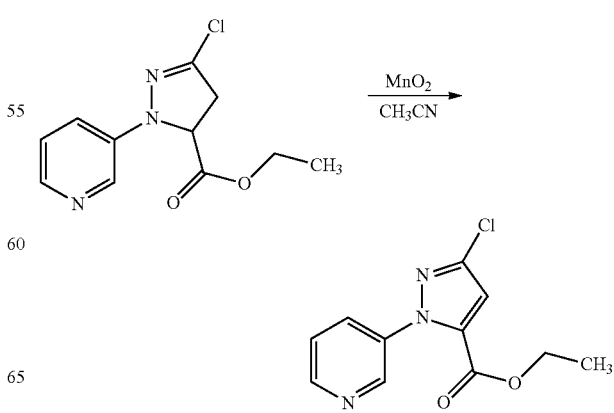

A 3-neck round bottomed flask (100 mL) was charged with ethyl 3-chloro-1-(pyridin-3-yl)-1H-dihydropyrazole-5-carboxylate (2.00 g, 7.88 mmol) and acetonitrile (20 mL). Manganese(IV) oxide (3.43 g, 39.4 mmol) was added. The reaction was stirred at 60° C. for 18 h. Additional manganese (IV) oxide (3.43 g, 39.4 mmol) was added and the reaction was stirred at 80° C. for 6 h. The mixture was filtered through a Celite® pad and the pad was rinsed with ethyl acetate (20 mL). The combined filtrates were concentrated to dryness and the residue was purified by flash column chromatography using 10-60% ethyl acetate/hexanes. The pure fractions were concentrated to dryness to afford a white solid after drying (1.84 g, 93%): $^1$H NMR (400 MHz, CDCl$_3$) δ 8.75-8.64 (m, 2H), 7.79 (ddd, J=8.2, 2.6, 1.5 Hz, 1H), 7.42 (ddd, J=8.2, 4.8, 0.8 Hz, 1H), 6.98 (s, 1H), 4.27 (q, J=7.1 Hz, 2H), 1.27 (t, J=7.1 Hz, 3H); $^{13}$C NMR (101 MHz, CDCl$_3$) δ 157.90, 149.88, 147.01, 141.41, 136.24, 135.27, 133.34, 123.11, 111.97, 61.87, 13.98; ESIMS m/z 252 ([M+H]$^+$).

Alternate Synthetic Route to Ethyl 3-chloro-1-(pyridin-3-yl)-1H-pyrazole-5-carboxylate (10c)

A vial (20 mL) was charged with ethyl 3-chloro-1-(pyridin-3-yl)-1H-dihydropyrazole-5-carboxylate (0.500 g, 1.97 mmol) and acetonitrile (5 mL). Sodium persulfate (0.799 g, 2.96 mmol) was added, followed by sulfuric acid (0.733 g, 7.88 mmol) (Exotherm!). The reaction was heated at 60° C. for 18 hours. The reaction was cooled to 20° C. and poured into water (20 mL). The mixture was treated with sodium carbonate to achieve pH 9 and extracted with ethyl acetate (2×20 mL). The organic layers were concentrated to a residue, which was purified by flash column chromatography using 50% ethyl acetate/hexanes as eluent to provide the title compound as a white solid (0.280 g, 56%).

4. Preparation of 3-chloro-1-(pyridin-3-yl)-1H-pyrazole-5-carboxylic Acid Hydrochloride (10d)

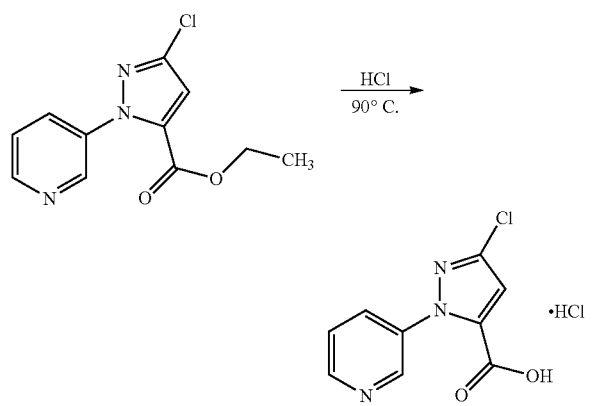

A 3-neck round bottomed flask (100 mL) was charged with ethyl 3-chloro-1-(pyridin-3-yl)-1H-pyrazole-5-carboxylate (0.200 g, 0.795 mmol) and hydrochloric acid (37%, 4 mL). The reaction was heated at 90° C. for 18 hours and allowed to cool to 20° C. Dioxane (5 mL) was added to the resulting suspension and was concentrated to dryness. Dioxane (5 mL) was added and the suspension was concentrated again to afford a white solid. Dioxane (5 mL) was added and the resulting suspension was stirred for 1 hour at 20° C. The solid was filtered and the solid was rinsed with dioxane (2 mL). The filter cake was dried under vacuum at 20° C. to afford the title compound as a white solid (0.218 g, 100%): $^1$H NMR (400 MHz, DMSO-d$_6$) δ 9.05 (dd, J=2.5, 0.7 Hz, 1H), 8.84 (dd, J=5.3, 1.4 Hz, 1H), 8.41 (ddd, J=8.3, 2.5, 1.4 Hz, 1H), 7.88 (ddd, J=8.3, 5.2, 0.7 Hz, 1H), 7.26 (s, 1H); $^{13}$C NMR (101 MHz, DMSO-d$_6$) δ 158.71, 146.00, 143.44, 140.36, 137.76, 137.00, 136.83, 125.19, 111.71.

4. Preparation of 3-(3-chloro-1H-pyrazol-1-yl)pyridine (5b)

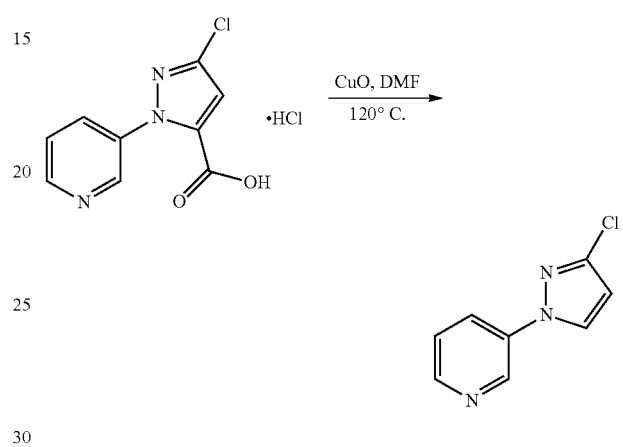

3-Chloro-1-(pyridin-3-yl)-1H-pyrazole-5-carboxylic acid hydrochloride (1.00 g, 3.65 mmol) was stirred in N,N'-dimethylformamide (10 mL). Copper (II) oxide (0.0580 mg, 0.730 mmol) was added and the reaction was heated at 120° C. for 16 hours, at which point the reaction was ~20% complete. Additional copper (II) oxide (0.112 g, 1.46 mmol) was added and the reaction was stirred for 5 hours. The mixture was diluted with ammonium hydroxide and water and extracted with ethyl acetate. The organic layer was washed with lithium chloride (15%) and concentrated to provide an orange solid. The residue was purified by flash column chromatography using ethyl acetate as eluent and the pure fractions were concentrated to afford the desired product as a white solid (0.481 g, 69.7%): mp: 66-68° C.; $^1$H NMR (400 MHz, CDCl$_3$) δ 8.93 (d, J=27 Hz, 1H), 8.57 (dd, J=4.8, 1.4 Hz, 1H), 8.02 (ddd, J=8.3, 2.7, 1.5 Hz, 1H), 7.91 (d, J=2.6 Hz, 1H), 7.47-7.34 (m, 1H), 6.45 (d, J=2.6 Hz, 1H); $^{13}$C NMR (101 MHz, CDCl$_3$) δ 148.01, 142.72, 140.12, 135.99, 128.64, 126.41, 124.01, 108.0.

Comparative Examples

Example CE-5 3-chloro-N-ethyl-1-(pyridin-3-yl)-1H-pyrazol-amine (5b)

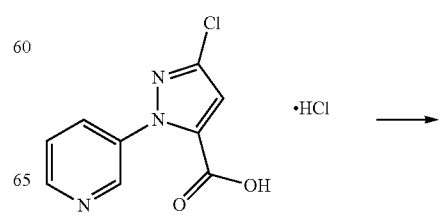

-continued

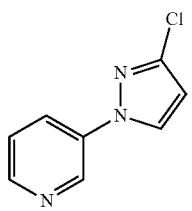

Attempted decarboxylation with sulfuric acid: 3-Chloro-1-(pyridin-3-yl)-1H-pyrazole-5-carboxylic acid hydrochloride (1.00 g, 2.50 mmol) was dissolved in warm sulfolane (12.5 mL). Sulfuric acid (1.35 mL, 25.0 mmol) was added and the reaction mixture was heated to 100° C. After stirring for 1 hour, LCMS indicated that the reaction did not occur. The reaction was further heated at 130° C. for 2 hours, at which point LCMS indicated no change. Additional sulfuric acid (4 mL) was added and the reaction was heated at 150° C. for 2 hours, at which point LCMS showed a new major peak that did not correspond to desired product.

Attempted decarboxylation with palladium(II) trifluoroacetate/trifluoroacetic acid: 3-Chloro-1-(pyridin-3-yl)-1H-pyrazole-5-carboxylic acid hydrochloride (1.00 g, 2.50 mmol) was dissolved in a mixture of dimethylsulfoxide (0.625 mL) and N,N'-dimethylformamide (11.9 ml). Trifluoroacetic acid (1.93 ml, 25.0 mmol) was added followed by the addition of palladium(II) trifluoroacetate/trifluoroacetic acid (0.332 g, 1.00 mmol). The reaction was heated at 100° C. overnight, at which time LCMS indicated that a reaction had occurred but no desired product had been formed.

Biological Examples

Example A Bioassays on Green Peach Aphid ("GPA") (*Myzus persicae*) (MYZUPE.)

GPA is the most significant aphid pest of peach trees, causing decreased growth, shriveling of leaves, and the death of various tissues. It is also hazardous because it acts as a vector for the transport of plant viruses, such as potato virus Y and potato leafroll virus to members of the nightshade/potato family Solanaceae, and various mosaic viruses to many other food crops. GPA attacks such plants as broccoli, burdock, cabbage, carrot, cauliflower, daikon, eggplant, green beans, lettuce, macadamia, papaya, peppers, sweet potatoes, tomatoes, watercress and zucchini among other plants. GPA also attacks many ornamental crops such as carnations, chrysanthemum, flowering white cabbage, poinsettia and roses. GPA has developed resistance to many pesticides.

Several molecules disclosed herein were tested against GPA using procedures described below.

Cabbage seedling grown in 3-in pots, with 2-3 small (3-5 cm) true leaves, were used as test substrate. The seedlings were infested with 20-5-GPA (wingless adult and nymph stages) one day prior to chemical application. Four pots with individual seedlings were used for each treatment. Test compounds (2 mg) were dissolved in 2 mL of acetone/MeOH (1:1) solvent, forming stock solutions of 1000 ppm test compound. The stock solutions were diluted 5× with 0.025% Tween 20 in water to obtain the solution at 200 ppm test compound. A hand-held aspirator-type sprayer was used for spraying a solution to both sides of the cabbage leaves until runoff. Reference plants (solvent check) were sprayed with the diluent only containing 20% by volume acetone/MeOH (1:1) solvent. Treated plants were held in a holding room for three days at approximately 25° C. and ambient relative humidity (RH) prior to grading. Evaluation was conducted by counting the number of live aphids per plant under a microscope. Percent Control was measured by using Abbott's correction formula (W. S. Abbott, "A Method of Computing the Effectiveness of an Insecticide" J. Econ. Entomol 18 (1925), pp. 265-267) as follows.

Corrected % Control=100*(X−Y)/X where

X=No. of live aphids on solvent check plants and

Y=No. of live aphids on treated plants

The results are indicated in the table entitled "Table 1: GPA (MYZUPE) and sweetpotato whitefly-crawler (BEMITA) Rating Table".

Example B Bioassays on Sweetpotato Whitefly Crawler (*Bemisia tabaci*) (BEMITA.)

The sweetpotato whitefly, *Bemisia tabaci* (*Gennadius*), has been recorded in the United States since the late 1800s. In 1986 in Florida, *Bemisia tabaci* became an extreme economic pest. Whiteflies usually feed on the lower surface of their host plant leaves. From the egg hatches a minute crawler stage that moves about the leaf until it inserts its microscopic, threadlike mouthparts to feed by sucking sap from the phloem. Adults and nymphs excrete honeydew (largely plant sugars from feeding on phloem), a sticky, viscous liquid in which dark sooty molds grow. Heavy infestations of adults and their progeny can cause seedling death, or reduction in vigor and yield of older plants, due simply to sap removal. The honeydew can stick cotton lint together, making it more difficult to gin and therefore reducing its value. Sooty mold grows on honeydew-covered substrates, obscuring the leaf and reducing photosynthesis, and reducing fruit quality grade. It transmitted plant-pathogenic viruses that had never affected cultivated crops and induced plant physiological disorders, such as tomato irregular ripening and squash silverleaf disorder. Whiteflies are resistant to many formerly effective insecticides.

Cotton plants grown in 3-inch pots, with 1 small (3-5 cm) true leaf, were used at test substrate. The plants were placed in a room with whitely adults. Adults were allowed to deposit eggs for 2-3 days. After a 2-3 day egg-laying period, plants were taken from the adult whitefly room. Adults were blown off leaves using a hand-held Devilbliss sprayer (23 psi). Plants with egg infestation (100-300 eggs per plant) were placed in a holding room for 5-6 days at 82° F. and 50% RH for egg hatch and crawler stage to develop. Four cotton plants were used for each treatment. Compounds (2 mg) were dissolved in 1 mL of acetone solvent, forming stock solutions of 2000 ppm. The stock solutions were diluted 10× with 0.025% Tween 20 in water to obtain a test solution at 200 ppm. A hand-held Devilbliss sprayer was used for spraying a solution to both sides of cotton leaf until runoff. Reference plants (solvent check) were sprayed with the diluent only. Treated plants were held in a holding room for 8-9 days at approximately 82° F. and 50% RH prior to grading. Evaluation was conducted by counting the number of live nymphs per plant under a microscope. Pesticidal activity was measured by using Abbott's correction formula (see above) and presented in Table 1.

TABLE 1

GPA (MYZUPE) and sweetpotato whitefly-
crawler (BEMITA) Rating Table

| % Mortality | Rating |
|---|---|
| 80-100 | A |
| More than 0-Less than 80 | B |
| Not Tested | C |
| No activity observed in this bioassay | D |

TABLE 2

| Example Compound | BEMITA | MYZUPE |
|---|---|---|
| 10a | B | B |
| 10b | B | B |

What is claimed is:

1. A process for preparing an alkyl 3-chloro-1-(pyridin-3-yl)-1H-pyrazole-5-carboxylate (10c)

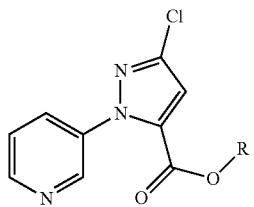

(10c)

comprising
treating the alkyl 3-chloro-1-(pyridin-3-yl)-4,5-dihydro-1H-pyrazole-5-carboxylate (10b)

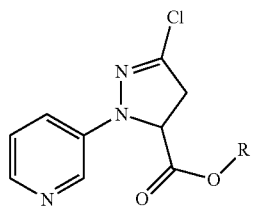

(10b)

with an oxidant in an inert organic solvent at a temperature of about 25° C. to about 100° C., wherein R is $(C_1-C_4)$ alkyl.

2. The process of claim 1, wherein the oxidant is manganese (IV) oxide or sodium persulfate/sulfuric acid.

3. The process of claim 1, wherein the amount of oxidant is about a 1.5 fold to about a 15 fold excess.

4. The process of claim 1, wherein the step of treating is performed in an organic solvent that is inert to the oxidant.

5. The process of claim 4, wherein the organic solvent is acetonitrile.

6. The process of claim 2, wherein the oxidant is manganese (IV) oxide.

7. The process of claim 2, wherein the oxidant is sodium persulfate/sulfuric acid.

8. The process of claim 7, wherein the organic solvent is acetonitrile.

9. The process of claim 4, wherein the organic solvent is a nitrile solvent.

10. The process of claim 1, wherein the oxidant is manganese (IV) oxide, the organic solvent is acetonitrile, and the reaction is carried out at a temperature of about 60° C.

11. The process of claim 1, wherein the oxidant is sodium persulfate/sulfuric acid, the organic solvent is acetonitrile, and the reaction is carried out at a temperature of about 60° C.

* * * * *